United States Patent [19]
Granz et al.

[11] Patent Number: 5,017,775
[45] Date of Patent: May 21, 1991

[54] OPTICAL APPARATUS FOR DETECTING CAVITATION BUBBLES IN LIQUIDS

[75] Inventors: Bernd Granz, Oberasbach; Ralf Holzapfel, Braeuningshof; Joachim Niewisch, Nuremberg, all of Fed. Rep. of Germany

[73] Assignee: Siemens Aktiengesellschaft, Berlin & Munich, Fed. Rep. of Germany

[21] Appl. No.: 494,757

[22] Filed: Mar. 16, 1990

[30] Foreign Application Priority Data

Mar. 23, 1989 [EP] European Pat. Off. ............ 89105282

[51] Int. Cl.⁵ ................................................. H01J 5/16
[52] U.S. Cl. ................................ 250/227.25; 250/574
[58] Field of Search ..................... 250/227.21, 227.25, 250/573, 574; 356/342; 73/861.42, 293

[56] References Cited

U.S. PATENT DOCUMENTS 3,564,264 2/1971 Karuhn et al. ..................... 250/574
4,659,218 4/1987 de Lasa et al. ..................... 250/574

Primary Examiner—David C. Nelms
Assistant Examiner—K. Shami
Attorney, Agent, or Firm—Kenyon & Kenyon

[57] ABSTRACT

An optical apparatus which includes an optical waveguide with an unattached end and a control and evaluation circuit for detecting a cavitation signal caused by the accumulation of cavitation bubbles at the unattached end is used to detect cavitation bubbles such as occur when shock waves pass through liquids.

8 Claims, 1 Drawing Sheet

OPTICAL APPARATUS FOR DETECTING CAVITATION BUBBLES IN LIQUIDS

BACKGROUND OF THE INVENTION

This invention relates to an optical apparatus in general and more particularly to an optical apparatus for detecting cavitation bubbles in liquids.

Cavitation occurs when shock waves of sufficiently low pressure pass through a liquid. It also occurs in extremely fast liquid flows in the liquid itself, or it may occur on boundary surfaces. The cavitation bubbles that form collapse after a short time. When they collapse, damage may occur on the surfaces on which the bubbles have settled. To avoid undesirable damage, it is necessary to detect the formation and progress of these cavitation bubbles and to monitor them.

An example where the use of ultrasonic shock waves with steep pulse edges leads to the formation of cavitation bubbles is found in lithotripters. Lithotripters are used to disintegrate calculi, such as kidney stones, which are found in the body of a patient. Therefore, one must monitor the occurrence of cavitation effects in the sonic field, which in this example means they must be monitored inside the body.

One way of detecting cavitation bubbles is by direct optical observation with the aid of a high-speed camera. Such a method is costly, however, and can only be used for optically transparent liquids. Also, it is not practical for applications involving continuous operation.

An apparatus for detecting cavitation bubbles is disclosed in *Collapse of Multiple Gas Bubbles by a Shock Wave and Induced Impulsive Pressure*, Y. Tomita et al., J. Appl. Phys. 56 (1), 1984, pp 125 to 131, where the ultrasonic pulse emitted by a collapsing cavitation bubble is measured. However, this method is not suitable for lithotripters, because the ultrasonic pulse that is emitted has only a small amplitude and it is difficult to separate from the reflected shock wave which is damping out.

In view of the prior art, there is a need for an apparatus for detecting cavitation bubbles in liquids that is inexpensive and with which it is possible to prove with certainty the existence of cavitation bubbles, even in the presence of a disturbing ultrasonic background.

SUMMARY OF THE INVENTION

According to the present invention, this task is accomplished by an optical apparatus that includes an optical waveguide having an unattached first end and a second end. The second end is optically coupled to a light source and to an opto-receiver. The opto-receiver has means for detecting a cavitation signal caused by the accumulation of cavitation bubbles at the unattached first end.

The cavitation bubbles forming near the unattached end of an optical waveguide diffuse to the surface of this optical waveguide and settle on its unattached end. As a result, the refractive index of the medium surrounding the optical waveguide is altered and thus the intensity of the light that is reflected into the optical waveguide at its unattached end is changed as well.

The apparatus of the present invention can be easily miniaturized, permitting measurements to be made at locations that are quite inaccessible, such as in the body of a patient when making an endoscopic measurement, for example.

An apparatus is disclosed in J. Staudenraus, W. Eisenmenger, *Optisches Sondenhydrophon*, Fortschritte der Akustik (*Optical Probe Hydrophone*, Advances in Acoustics), DAGA 1988, DPG GmbH, p. 467, where the content of an optical signal reflected from the exposed end of an optical waveguide is used to measure the pressure of ultrasonic shock waves in a liquid as a function of time. This known apparatus utilizes the principle that the high compression amplitude of the shock wave in the immediate vicinity of the optical waveguide tip produces a change in the density of the liquid and thus a change in the refractive index of the liquid. This change in the refractive index modulates a fraction of the light reflected back into the optical waveguide. The diameter of the optical waveguides used for the measurement does not exceed 0.1 mm. In an apparatus disclosed in J. Staudenraus, W. Eisenmenger, *Optical Probe Hydrophone*, seminar volume, AMA seminar; *Fiber and Integrated Optical Sensors*, ACS Organisations GmbH, Wunstorf, 1988, pp 67 to 73, a core diameter of 0.2 mm is indicated for the optical fibers. Cavitation bubbles were observed with both of the above apparatuses, however they were noticeable only as fluctuations in the intensity of the reflected light.

The present invention is based on the realization that the detection of cavitation bubbles that have formed in the liquid can only be proven with certainty when they are deposited on the unattached end of an optical waveguide. Only in this case is a signal received which is correlated with the shock wave both in time as well as with regard to its amplitude, and which thus can be clearly interpreted as a cavitation signal. This cavitation signal can be detected by suitable means connected to the opto-receiver and it can be used both to display a cavitation effect as it occurs as well as to analyze the lifetime of the cavitation bubbles.

An accumulation of cavitation bubbles at the exposed end of the optical waveguide is facilitated when the exposed end has a flat cross-sectional area that is larger than 0.2 $mm^2$. The exposed end of the optical waveguide is preferably formed by a flat end face, which is oriented approximately perpendicular to the longitudinal axis of the optical waveguide.

The optical waveguide is advantageously composed of a polymer, in particular, polymethylmeth acrylate PMMA. Optical waveguides made of PMMA are less sensitive to the damaging effects of shock waves than are optical waveguides made of glass.

Cylindrical fibers with diameters greater than 0.5 mm are particularly advantageous as optical waveguides.

The change in the reflectivity of the boundary surface between the exposed end of the optical waveguide and the liquid, which is caused by the cavitation bubbles, is distinguished from the shock wave signal by its amplitude and its polarity. Thus, the occurrence of cavitation bubbles can be easily recognized in an evaluation circuit that is connected to the opto-receiver.

DETAILED DESCRIPTION

Figure 1:
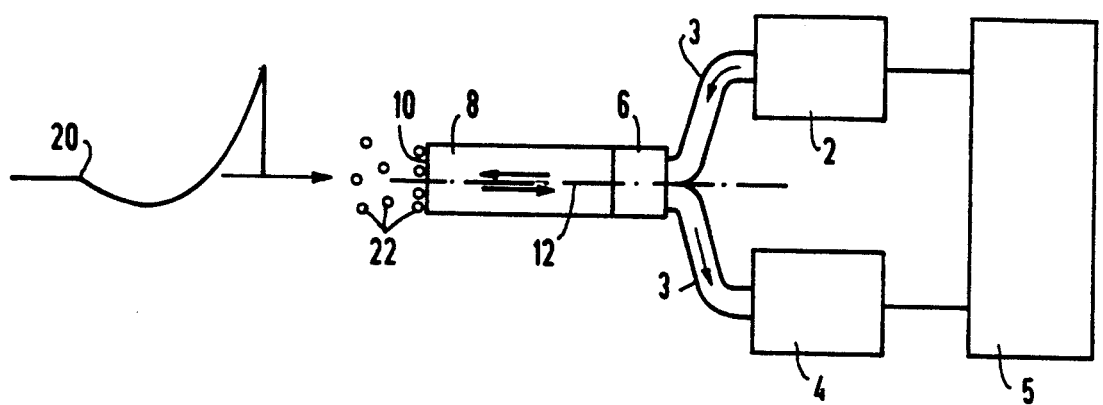
FIG. 1 schematically illustrates the optical apparatus of the present invention.

FIG. 1 shows a light source 2 and an opto-receiver 4 that are optically coupled via optical fibers 3 and a y-coupler 6 to an optical waveguide 8. The light source 2 may be a laser diode and the opto-receiver 4 may be a photodiode, for example. The optical waveguide 8 has a flat end face at its unattached end 10 which is on the side opposite from the y-coupler 6. This end face at the unattached end 10 is preferably arranged perpendicular to the longitudinal axis 12 of the optical waveguide 8. As a result of the flat shape of the exposed end 10 of the optical waveguide 8, the accumulation of cavitation bubbles 22 caused by a shock wave 20 is facilitated. The shock wave is shown schematically as a function of time in FIG. 1. In the embodiment illustrated, the optical waveguide 8 is made of a polymer, specifically polymethylmeth acrylate (PMMA). The cross-sectional area of the exposed end face 10 is preferably greater than 0.2 $mm^2$, and more preferably it is greater than 0.5 $mm^2$. A cylindrical fiber having a diameter greater than 0.5 mm is particularly suited as an optical waveguide 8.

When a shock wave 20 passes through the liquid, cavitation bubbles 22 are produced. These bubbles 22 are deposited on inhomogeneities in the liquid and as well as on the unattached end 10 of the optical waveguide 8. As a result, the [optical]reflectivity of the boundary surface between the optical waveguide 8 and the liquid is clearly increased and thus the opto-receiver 4 continues to receive light of high intensity until the cavitation bubbles 22 at the exposed end 10 collapse. By measuring the reflectivity of this boundary surface, not only can the formation of cavitation bubbles 22 be established, but their lifetimes can be determined as well. The free cavitation bubbles 22 found in the liquid essentially do not contribute to the signal that is received at the opto-receiver 4, since the fraction of light which is reflected into the optical waveguide 8 by diffuse reflection is insignificant.

The light source 2 and the opto-receiver 4 are connected to a control and evaluation unit 5. This unit 5 performs an analysis to determine if the signal measured by the opto-receiver 4 contains a cavitation signal, indicating the existence of cavitation bubbles 22. Because of the characteristics of the cavitation signal that occurs in conjunction with the cavitation bubbles 22, the cavitation signal can be easily detected using suitable means. The control and evaluation unit 5 may include such means. For example, unit 5 may include means by which the shock-wave signal measured at the opto-receiver 4 can be differentiated from the cavitation signal. This can be accomplished, for example, by a comparator circuit arrangement, which measures the amplitude of the signal at the opto-receiver 4 and compares it to a specified threshold value. The shock-wave signal which occurs before the cavitation signal can be used effectively as a reference signal for time and amplitude values. For example, only those measured signals which occur within a specified period of time after the measurement of the shock-wave signal can be considered cavitation signals.

Figure 2:
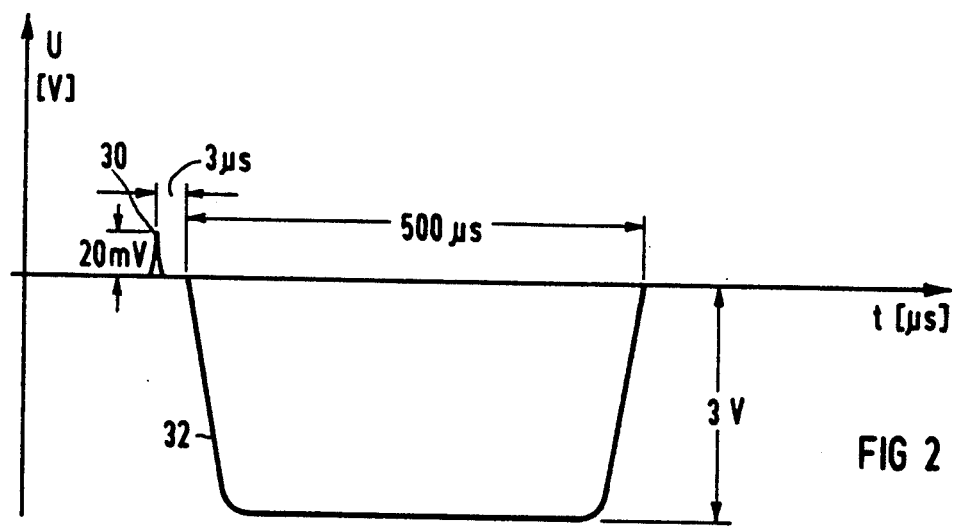
FIG. 2 shows an output signal as a function of time resulting from the formation of cavitation bubbles, which is measured by the opto-receiver of the present invention.

FIG. 2 shows the typical behavior of the electrical signal as a function of time, which is measured at the opto-receiver 4. This measurement was made with a 1 mm-diameter optical waveguide made of PMMA. A laser diode with a power of 5 mW was used as a light transmitter. After the shock-wave signal 30 occurs, which has an amplitude of approximately 20 mV in the apparatus used, a cavitation signal 32 is observed which has a polarity opposite of the shock-wave signal 30. The amplitude of the cavitation signal 30 is approximately 100 times the amplitude of the shock-wave signal 30 and it lasts about 500 usec, which is when the cavitation bubbles collapse. The difference in polarity between the shock-wave signal 30 and the cavitation signal 32 is due to the fact that the shock-wave signal 30 is caused by an increase in the refractive index of the liquid, while the cavitation signal 32 is caused by a reduction in the refractive index in the vicinity of the exposed end of the optical waveguide 8. The cavitation signal 32 can be clearly distinguished from the shock-wave signal 30, both by its behavior as a function of time, as well as by its polarity and its amplitude.

What is claimed is:

1. An optical apparatus for detecting cavitation bubbles caused by a shock wave in liquids comprising:
    (a) an optical waveguide having an unattached first end and a second end;
    (b) a light source optically coupled to said second end;
    (c) an opto-receiver also optically coupled to said second end;
    (d) means for detecting a shock wave signal and a cavitation signal resulting from the accumulation of the cavitation bubbles at said unattached first end coupled to said opto-receiver so that the presence of cavitation bubbles caused by the shock wave can be determined.

2. The optical apparatus of claim 1, wherein said unattached first end of said optical waveguide comprises a flat end face oriented approximately perpendicular to the longitudinal axis of said optical waveguide.

3. The optical apparatus of claim 2, wherein the cross-sectional area of said end face is at least 0.2 $mm^2$.

4. The optical apparatus according to claim 3, wherein said optical waveguide is cylindrical with a cross-sectional diameter of at least 0.5 mm.

5. The optical apparatus according to claim 1, wherein said optical waveguide is composed of polymethylmeth acrylate PMMA.

6. The optical apparatus according to claim 2, wherein said optical waveguide is composed of polymethylmeth acrylate PMMA.

7. The optical apparatus according to claim 3, wherein said optical waveguide is composed of polymethylmeth acrylate PMMA.

8. The optical apparatus according to claim 4, wherein said optical waveguide is composed of polymethylmeth acrylate PMMA.

* * * * *